United States Patent [19]

Reich

[11] Patent Number: 4,551,627

[45] Date of Patent: Nov. 5, 1985

[54] METHODS AND APPARATUS FOR DETECTING RESIDUAL LIQUID IN CONTAINERS

[75] Inventor: Frederich R. Reich, Richland, Wash.

[73] Assignee: Kirin Beer Kabushiki Kaisha, Tokyo, Japan

[21] Appl. No.: 518,934

[22] Filed: Aug. 1, 1983

[51] Int. Cl.[4] ............................ G01F 23/28; G01J 5/48
[52] U.S. Cl. ..................................... 250/339; 250/301; 250/341; 250/223 B
[58] Field of Search ..................... 250/339, 223 B, 341, 250/343, 301, 349; 209/588, 582, 577; 356/240

[56] References Cited

U.S. PATENT DOCUMENTS

| | | | |
|---|---|---|---|
| 3,454,759 | 7/1969 | Calhoun | 250/338 |
| 4,121,103 | 10/1978 | Calhoun | 250/343 |
| 4,221,961 | 9/1980 | Peyton | 250/223 B |
| 4,236,075 | 11/1980 | Nexo et al. | 250/343 |
| 4,236,076 | 11/1980 | Judge et al. | 250/347 |
| 4,368,980 | 1/1983 | Aldred et al. | 356/240 |

FOREIGN PATENT DOCUMENTS

| | | | |
|---|---|---|---|
| 27918 | 2/1980 | Japan | 356/240 |
| 2119928 | 11/1983 | United Kingdom | 356/240 |

*Primary Examiner*—Alfred E. Smith
*Assistant Examiner*—Constantine Hannaher
*Attorney, Agent, or Firm*—Koda and Androlia

[57] ABSTRACT

Optical transmittances of a combination of a liquid to be detected and a container wall are measured in order to select two optical pass-bands, one of which is relatively high transmittance level while the other of which is relatively low transmittance. The light transmission quantities of the container at the selected two pass-bands are measured by one or more detecting elements. The light transmission quantities are converted into two electric signals, one of which is divided by the other in a signal process circuit.

9 Claims, 15 Drawing Figures

METHODS AND APPARATUS FOR DETECTING RESIDUAL LIQUID IN CONTAINERS

BACKGROUND OF THE INVENTION

This invention relates to methods and apparatus for inspecting residual liquid such as water, oil, and liquid soap in empty washed food and beverage containers, in particular, refillable beverage containers.

In general, it is desired to reuse food and beverage containers for economical sake and required to wash the containers with water or soap to remove residual liquid or dirty things therefrom before the containers will be refilled with food or beverage. After the washing processes, since remaining liquids such as water, oil, and liquid soap may exist further in the containers, these residual liquids should be completely detected and removed before the refilling processes.

Furthermore, beverage containers returned back to a refilling factory from sellers and markets may be contaminated with residual cooking oil and motor oil. Such containers have to be disposed of before their washing processes because these materials are difficult to remove completely in conventional washing processes and, in fact, the washing processes may spread these materials to other containers.

To reject such containers containing excess water or oil, the refillable beverage containers are normally detected in two positions in a container process line by using electro-optic inspectors.

U.S. Pat. No. 4,221,961 discloses one of electro-optic inspectors, in particular, a bottle inspector. The known bottle inspector is so constructed that it can detect particles and liquid in a bottle. It has a light source located under the bottle bottom, a rotatable scanner head located over the bottle neck to receive light passing through the bottle bottom from the light source, and a detector for receiving light reflected by the surface of the scanner head to detect only particulate matters on the bottle bottom. The scanner has reflecting segments and non-reflecting portions. The reflecting segments reflect the light passing through the bottle bottom so as to focus a bottle bottom image onto the detector. If there are particulate matters on the bottle bottom, they block the light from the light source to cause a dip in detector output. The non-reflecting portions are provided with an infrared detector for detecting the infrared radiation passing through the bottle bottom. The light to be received by the infrared detector is filtered so that only light having wavelengths in or near one of the absorption bands of liquid can pass therethrough to reach the infrared detector. If there is liquid in the bottle bottom, the light is partially absorbed to cause a dip in A.C. coupled amplitude of the infrared detector providing an indication of the presence of the liquid.

This is liquid detection is based on the fact that the light in the near infrared wavelength range is greatly absorbed when it passes through liquid such as water, oil or the like. However, the light from the light source is also absorbed by a bottle wall in addition to the liquid in the bottle. Optical transmittance varies also with thickness or color of the bottle wall as well as kind or quantity of liquid. In case that the quantity of liquid is very small, the thickness or color of the bottle wall may have more influence on the optical transmittance than the presence of liquid. For this reason, the known detector can detect the presence of liquid in only the case of relatively large amount of liquid existing in the container. Because, at this time, other interfering components such as the bottle wall will be able to be neglected. However, a small quantity of liquid cannot be effectively detected by means of the known detector for the above reason. Even if the quantity of liquid such as water, oil or liquid soap in the bottle bottom is small, it affects human taste sensitivity and food or beverage quality in the containers. In addition, the oil or soap may cause a health hazard.

SUMMARY OF THE INVENTION

It is an object of the present invention to provide an improved method and apparatus in which small quantities of liquid such as water, oil or soap in containers can be completely detected to remove the containers containing such harmful residues from a refillable container process line.

According to one aspect of this invention, there is provided a method for detecting of residual liquid such as water, liquid soap or oil in containers, comprising the steps of: measuring optical transmittances of a combination of one kind of liquid to be detected and a container wall in which the liquid is accommodated; selecting two optical pass-bands, one of which is relatively high transmittance level with respect to the liquid to be detected while the other of which is relatively low transmittance level with respect to the liquid to be detected; measuring light quantities at the two optical pass-bands when light passes through the bottom and neck of the container; converting the light quantities into respective two electric signals; and comparing one electric signal with respect to one pass-band with the other electric signal with respect to the other pass-band.

According to another aspect of this invention, there is provided a method for detection of residual liquid such as water, liquid soap or oil in containers wherein more than two kinds of liquids are accommodated in each container, comprising steps of: measuring optical transmittances of, a combination of liquid to be detected and a container wall and a combination of other liquid coexisting with the liquid to be detected and the container wall; selecting two optical pass-bands, one of which is relatively high transmittance level with respect to the liquid to be detected while the other of which is relatively low transmittance level with respect to the liquid to be detected, and each of which is equal in transmittance level to each other with respect to the combination of other liquid coexisting with the liquid to be detected and the container wall; measuring light quantities at the two optical pass-bands when light passes through the bottom and neck of the container; converting the light quantities into respective two electric signals; and comparing one electric signal with respect to one pass-band with the other electric signal with respect to the other pass-band.

According to still another aspect of this invention, there is provided an apparatus for detection of residual liquid such as water, liquid soap or oil in containers, comprising: a light source located under the bottom of a container to be detected; means for chopping the light from the light source and splitting it into two light beams; two filters located on the way of light path and having different pass-bands from each other, one of which has a pass-band in which light transmittance level is relatively high with respect to the liquid to be detected while the other of which has a pass-band in which light transmittance level is relatively low with respect to the liquid to be detected; at least one means for detecting the light beam which has passed through the container and has been chopped and splitted; a signal processor circuit in which each light quantity filtered by the two filters and received by the detecting element is converted into two electric signals which are compared with each other.

The nature, utility and further features of this invention will be more clearly apparent from the following detailed description with respect to a preferred embodiment of the invention when read in conjunction with the accompanying drawings.

DETAILED DESCRIPTION OF THE INVENTION

Figure 1:
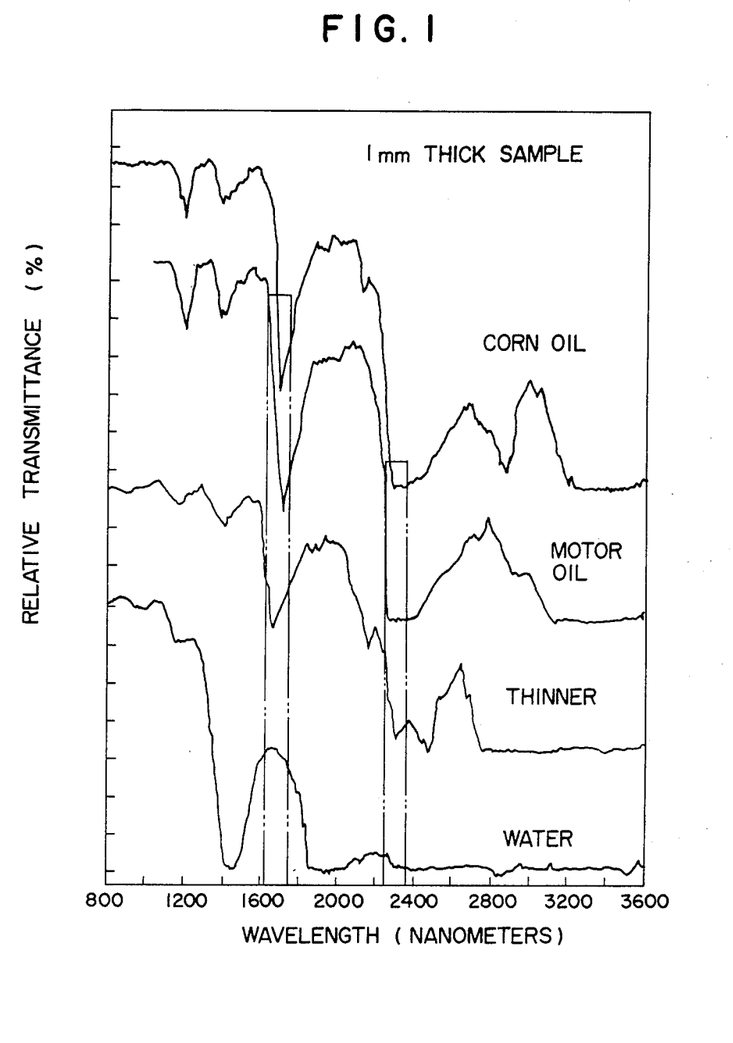
FIG. 1 is a diagram showing the respective transmittances of several typical liquids.

The subject of this invention is based on the selective absorption of optical energy for water, oil or liquid soap as shown in FIG. 1. In FIG. 1, relative transmittances of four materials such as corn oil, motor oil, thinner and water are shown with respect to each wavelength of light when it passes through the respective materials, each having thickness of 1 mm.

According to FIG. 1, it is seen that the infrared spectral absorption of these hydrocarbon materials exhibits a characteristic absorption fingerprint with a few strong absorption bands such as at around $1.7 \times 10^{-6}$ and $2.3 \times 10^{-6}$ meter wavelengths. In case of water, there will be observed a peak at around $1.7 \times 10^{-6}$ meter wavelength.

Figure 2:
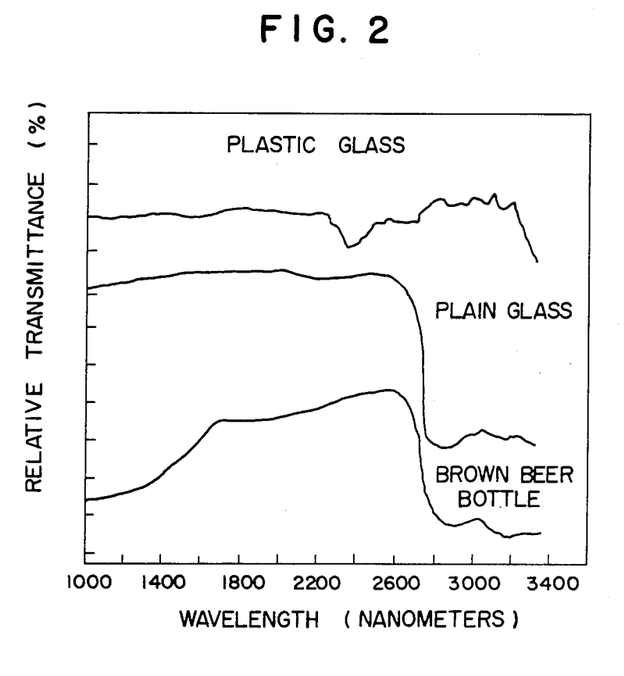
FIG. 2 is a diagram showing the respective transmittances of a few of glasses of containers.

FIG. 2 shows relative transmittance of containers for beverage or food such as a clear plastic bottle, a clear plain glass bottle or a brown beer bottle. In each container, there is observed no big change in transmittance within the wavelength range of about 1600 to 2600 nanometers.

When liquid in a bottle is detected, light emanated from a light source must pass through bottle wall and at this time, the bottle wall absorption significantly affects the detection sensitivity as the absorption is different for each bottle due to wall thickness or color variations and basic changes in bottle constituents.

Figure 3:
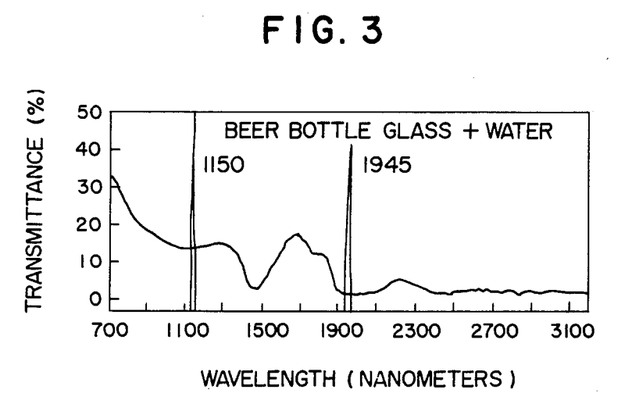
FIG. 3 is a diagram showing transmittances of a combination of water and a beer bottle glass.

FIG. 3 shows the optical spectra data of the transmittances of light when it passes through a combination of beer bottle glass and water. The data indicates that there are several regions where water and caustic or liquid soap absorbs optical energy, and the transmittance line almost corresponds to a combination of the line for water in FIG. 1 and the line for the brown beer bottle.

Figure 4:
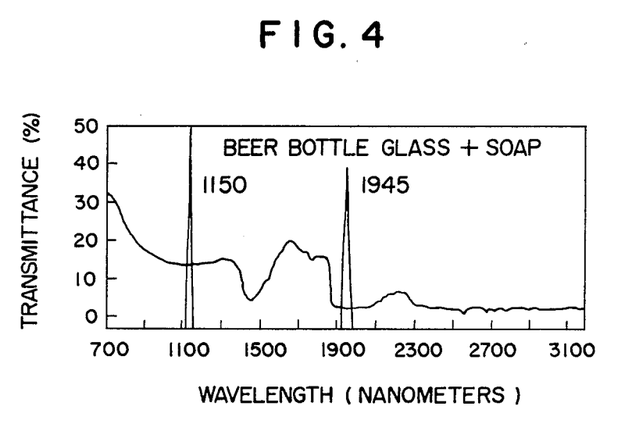
FIG. 4 is a diagram showing the transmittances of a combination of liquid soap and a beer bottle glass.

On the next step, with respect to a combination of the beer bottle glass and caustic, a test similar to that of transmittances for the above combination was made. The result is shown in FIG. 4. Comparing FIG. 3 with FIG. 4, it can be understood that transmission responses for water and caustic (liquid soap) are almost identical with each other.

In two transmittance lines in FIGS. 3 and 4, the transmittances are relatively stable at around the wavelengths of $1.15 \times 10^{-6}$ and $1.95 \times 10^{-6}$ meters. That is, the lines extend almost horizontally and there is observed no big change in transmittances at near the two wavelengths (optical pass-bands). At around the wavelength of $1.15 \times 10^{-6}$ meter, the transmittance is rather high while at the wavelength of $1.95 \times 10^{-6}$ meter, the transmittance is relatively low.

Accordingly, if two optical filters, one for transmitting light of only around the wavelength of, for example, $1.15 \times 10^{-6}$ meter and the other for transmitting light of only around the wavelength of, for example, $1.95 \times 10^{-6}$ meter are used, and the quantities of light having passed through the two filters for a predetermined period of time are compared with each other, the presence of water or liquid soap can be easily detected irrespective of the bottle thickness variations and the quantity of water or soap.

The filters to be used are not limited to the above ones but other filters for transmitting light of around other wavelengths can be used as long as the transmittances at the two optical pass-bands to be selected are greatly different from each other.

Likewise, if, with respect to a combination of a beer bottle glass and oil, the transmittances at each wavelength are measured thereby to select two optical pass-bands, and light transmittance quantities at the two pass-bands are compared with each other, any oil can be detected in the same manner.

A detector for implementing an optical energy comparison in two optical pass-bands now will be explained hereinbelow with respect to mainly FIG. 5.

Figure 5:
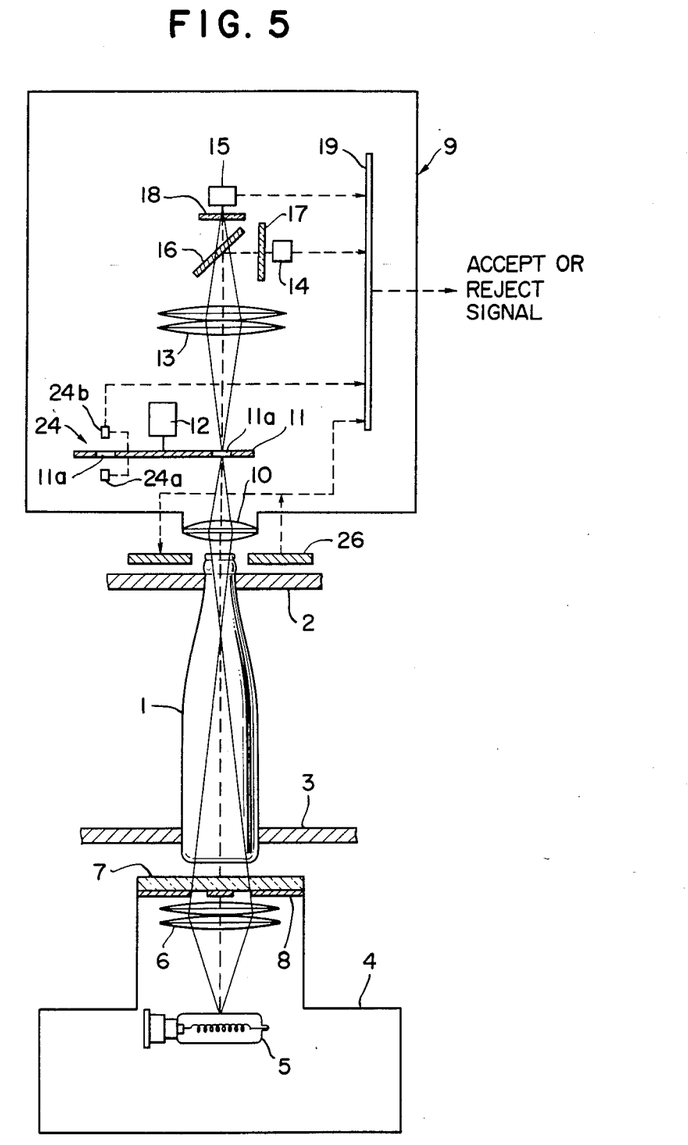
FIG. 5 is a diagrammatical view showing a detector for detecting water or oil in a beer bottle.

In FIG. 5, a beer bottle 1 is supported, at its neck and bottom portion, respectively, by supporting plates 2 and 3. Under the bottle bottom is provided a light source box 4 having a tungsten filament lamp 5 as a light source, a combination lens 6 for focusing the light from the lamp 5 in a position which is near the bottle neck in the bottle 1 after passing through the bottle bottom, a plain glass plate 7 and a shield plate 8 for permitting the light to pass through only the bottle bottom. Arc sources such as a Xenon or Hg arc lamp are potential illumination sources instead of the tungsten lamp as well as lasers and flash lamps.

A detector box 9 is provided over the bottle neck. A lens 10 is disposed to the detector box 9 at a position facing to the bottle neck so that the light passing through the neck is focused in a position where a chopper wheel 11 is located. The chopper wheel 11 is rotated by an electric motor 12 and provided with a plurality of holes 11a, for chopping the light focused by the lens 10, the holes 11a being arranged annularly with equal intervals in a circumferential direction. The chopping function is necessary for the reduction of noise.

Over the chopper wheel 11 is provided a combination lens 13 for focusing the light onto two detecting elements 14 and 15 through a beam splitter or half mirror 16 for directing the light toward two directions and two pass-band filters 17 and 18 provided between the beam splitter 16 and the respective detecting elements 14 and 15. The pass-band filters 17 and 18 limit the optical energy to be transmitted therethrough to specific spectral regions or pass-bands, respectively. For example, in case of the detection of water or soap, 1.15 and 1.95 nanometer pass-band filters are desirous of being selected as mentioned above.

Figure 6:
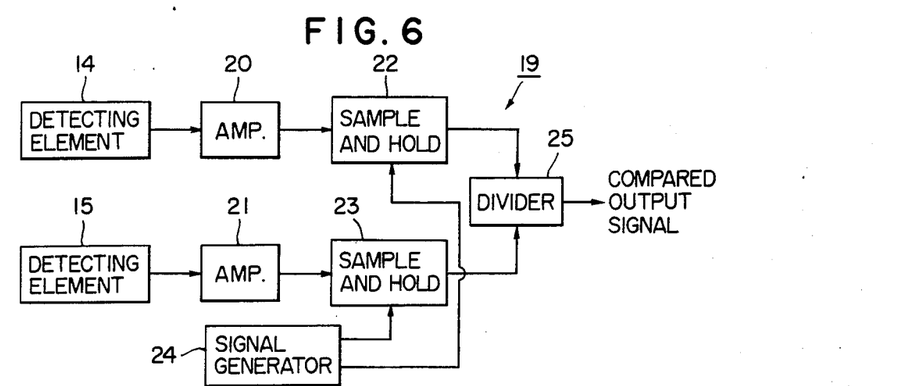
FIG. 6 is a block diagram showing a signal processor circuit for processing signals from detecting elements.

A signal processor circuit for processing output signals from the two detective elements 14 and 15 has two amplifier circuits 20 and 21 which are connected to the two detective elements 14 and 15, respectively as shown in FIG. 6. The detective element outputs are first amplified by those amplifier circuits 20 and 21 and then input to two sample and hold circuits 22 and 23, respectively, which are controlled by the mechanical chopper wheel 11. That is, in the vicinity of the chopper wheel 11 is provided a signal generator 24 comprising a light illuminating element 24a and a light receiving element 24b between which the chopper wheel 11 is located. When a light projected from the light illuminating element 24a passes through each hole 11a, the light receiving element 24b outputs a signal toward each of the sample and hold circuits 22 and 23 to cause them to respectively hold the signals from the detecting elements 14 and 15.

Thus, each of the sample and hold circuits 22 and 23 provides constant holding signals for a divider 25 which outputs the ratio of the two holding signals. If the ratio is 1, that indicates no water in the bottle thereby to give a non-reject (accept) signal to a bottle process line. However, if the ratio is not 1, for example, less than 1, the presence of water in the bottle is indicated thereby to give a reject-signal to the bottle process line.

Figure 7:
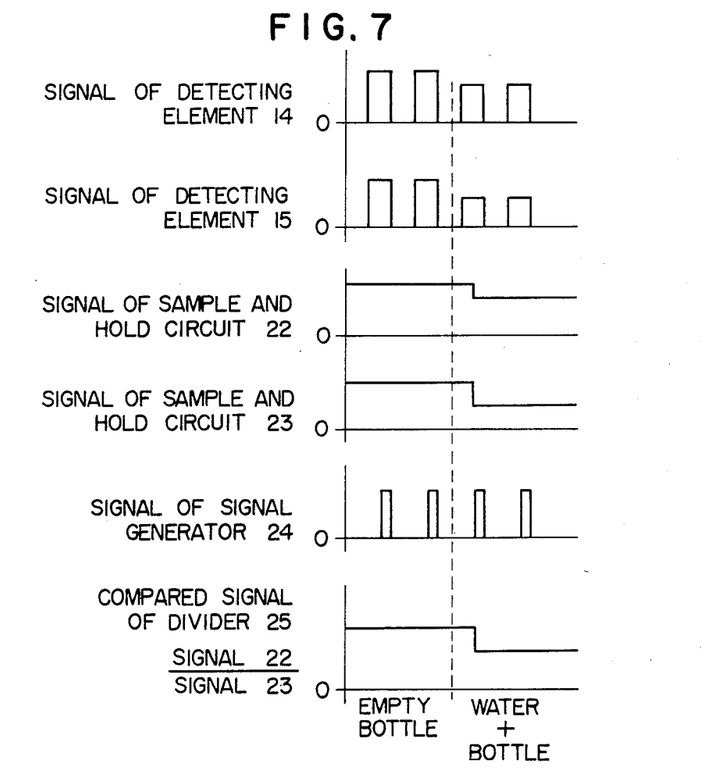
FIG. 7 is a sequence control diagram showing an operation of the signal processor circuit in case of detection of residual water.

The sequentail control of the signal processor circuit 19 is shown in FIG. 7.

With reference back to FIG. 5, in the vicinity of the bottle neck is provided a bottle presence detector 26 such as phototubes which outputs a bottle presence signal to the signal processor circuit 19.

Figure 8A:
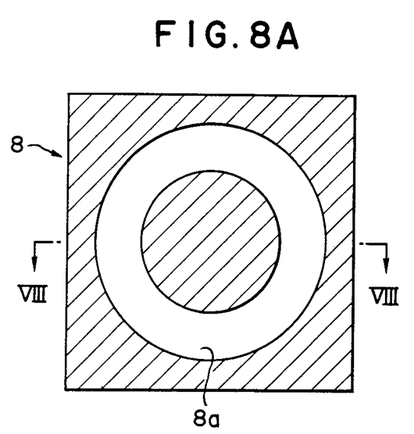
FIG. 8A is a plan view showing a shield plate for illuminating only the bottom of the bottle.
Figure 8B:
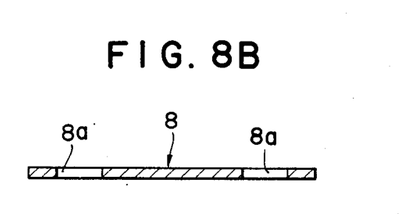
FIG. 8B is a sectional view taken along the line VIII—VIII of FIG. 8A.

Furthermore, the shield plate 8 has an annular aperture 8a, as shown in FIGS. 8A and 8B, through which the light from the lamp 5 passes thereby to illuminate only the inner circumferential parts 1a of the beer bottle bottom in which a small quantity of liquid L such as water, oil or liquid soap is apt to be resided.

Figure 9:
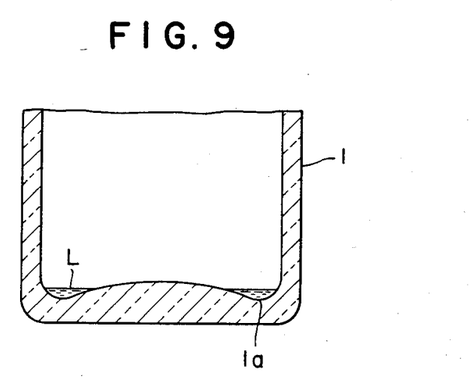
FIG. 9 is a sectional view, of the bottle bottom, showing the state where a small amount of liquid is left in the circumferential parts of the bottle bottom.

Most beverage bottles are formed with convex bottoms as illustrated in FIG. 9. In case of such beverage bottles, the shield plate 8 functions to optimize the detection sensitivity because it can prevent harmful diffused light from reaching the detecting elements 14 and 15.

Figure 10:
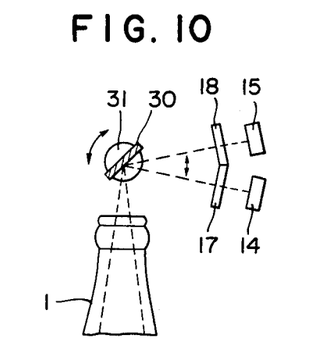
FIG. 10 is a diagrammatical view of a first modification of the detector in which a light chopping means is used in a different manner from that of FIG. 5.

FIG. 10 shows a first modification of the detector according to this invention. In FIG. 10, the chopping function is supplied by an oscillating mirror 30 which is driven by a torsional (oscillating) motor 31. The oscillating mirror 30 directs the optical beam alternately to each of the two detecting elements 14 and 15 disposed in predetermined angular positions through optical filters 17 and 18. This structure provides chopped signals, for the detecting elements 14 and 15, which also can be processed by the same signal processor circuit as that of FIG. 5.

Figure 11:
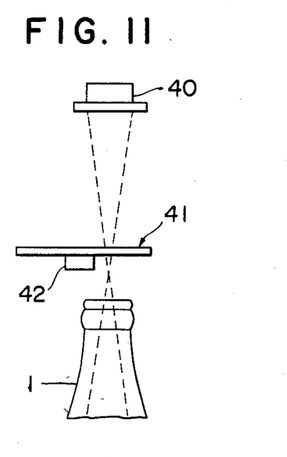
FIG. 11 is a view, similar to FIG. 10, showing a second modification of the detector in which other light chopping means is used.
Figure 12:
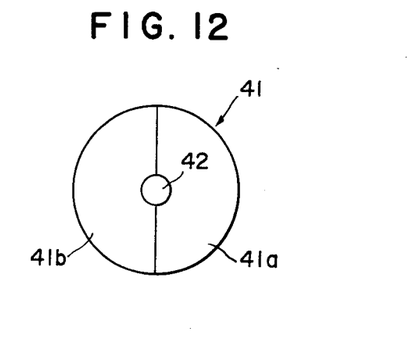
FIG. 12 is a plan view of a combination filter shown in FIG. 11.

A second modification of the detector according to this invention is shown in FIG. 11 in which only one detecting element 40 is used and a rotatable combination filter 41 is provided between the bottle neck and the detecting element 40. The combination filter 41 is formed by combining two semi-circular filter parts 41a and 41b which have different pass-bands respectively and rotated by a motor 42 at a predetermined speed. It functions to chop the light alternately with the filter parts 41a and 41b. In this case, as the detecting element 40 receives signals from both filter parts 41a and 41b, the signals are adapted to be separated from each other to be sent to two similar sample and hold circuit.

The water detecting capabilities of the detector according to this invention were tested with respect to 633 ml brown beer bottle. The sensitivity tests indicated that 100 percent rejection could only be obtained with water volumes greater than 5 ml. About 1.7 percent of the empty bottles were also rejected, but each of these bottles had a wedge bottom which affected the optical path through the bottle. With broader optical pass-band filters, the inspection sensitivity could be increased to 0.5–1.0 ml of water for bottles that do not have wedge bottoms because the broader optical pass-band filters can increase detector signals thereby to raise the signal-to-noise level.

In the above embodiments, a method and detector for detecting water or liquid soap which is independently left in a container are described. However, they can be applied to detection of oil in case of oil coexisting with water in a container.

Such a detection method or oil will now be explained hereinbelow.

In a beer bottle processing line where beer bottles are washed and rinsed, there may be a fear that oil such as corn oil or motor oil is left in some beer bottles with a small amount of residual water. Although extremely small amount of residual water is permissible, in case of oil, every beer bottle containing any oil should be rejected even if its amount is extremely small. Accordingly, it is important to detect whether or not, particularly, an oil exists with water in the beer bottles.

Figure 13:
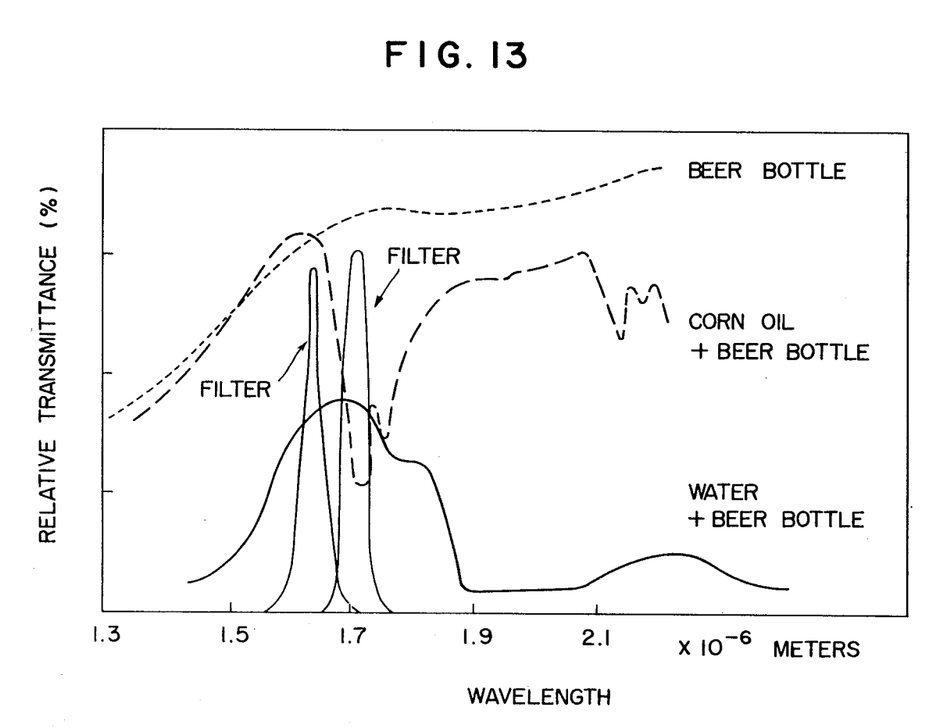
FIG. 13 is a graph representing the transmittances of a combination of a beer bottle and corn oil or water.

FIG. 13 shows relative optical transmittances, with respect to optical wavelengths, of a beer bottle, corn oil in a beer bottle and water in a beer bottle. All motor oils and cooking oils exhibit a strong absorption band at around $1.7 \times 10^{-6}$ meter wavelength as also shown in FIG. 1.

When the oil coexisting with water is detected, as a rule, the absorption of water and a beer bottle wall will interfere with the detection of the oil. However, at around $1.6 \times 10^{-6}$ and $1.7 \times 10^{-6}$ meter wavelengths, the transmittances of water plus the beer bottle are relatively high and have almost the same influence on those of oil plus the beer bottle.

Therefore, if two pass-bands, that is, one being about $1.6 \times 10^{-6}$ meter wavelength pass-band and the other being about $1.7 \times 10^{-6}$ meter wavelength pass-band, are selected, the absorption of water plus the beer bottle can be almost compensated for. In addition, the transmittances at the two pass-bands are extremely different. Therefore, by comparing the ratio of optical energy in these two optical pass-bands by means of the above detector, the detection for any oil can be attained.

Figure 14:
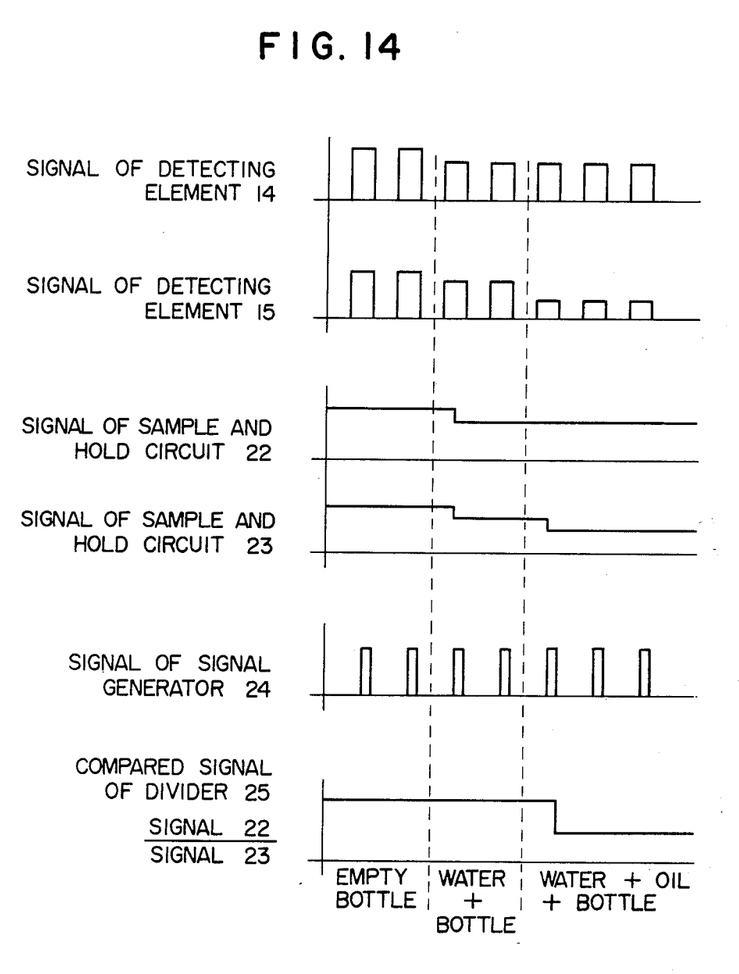
FIG. 14 is a sequence control diagram showing an operation of the signal processor circuit in case of detection of residual oil.

In this case, a sequence control of the signal process circuit 19 is described in FIG. 14.

In fact, 1.639 and $1.717 \times 10^{-6}$ meter pass-bands were used and they were effectively functioned. However, the selection of the pass-bands should not limit to the above wavelengths. Under other conditions, other combinations of optical pass-bands may be more effective for indicating the presence of particular oil in the presence of interfering materials such as water and liquid soap.

What we claim is:

1. A method for detecting residual oil coexisting with water in a container, comprising the steps of:
   (a) measuring optical transmittances of a combination of oil to be detected and a container wall and a combination of water coexisting with the oil to be detected and a container wall;
   (b) selecting two optical pass-bands, one of which is relatively high transmittance level with respect to combination of the oil and the container wall while the other of which is relatively low transmittance level with respect to the same, and each of which is almost equal in transmittance level to each other with respect to the combination of water coexisting with the oil to be detected and the container wall;
   (c) measuring light quantities at the two optical pass-bands when light passes through the bottom and necks of the container;
   (d) converting the light quantities into respective two electric signals; and
   (e) comparing one electric signal with respect to one pass-band with the other electric signal with respect to the other pass-band.

2. A method according to claim 1, wherein, as the two optical pass-bands, about $1.64 \times 10^{-6}$ and $1.72 \times 10^{-6}$ meter wavelengths are selected for detection of oil coexisting with water in a beer bottle.

3. An apparatus for detecting residual liquid such as water, liquid soap or oil in containers, comprising:
   (a) a light source located under the bottom of a container to be detected;
   (b) a rotatable chopper wheel with a plurality of holes located at predetermined intervals of length in its circumferential direction;
   (c) a beam splitter for directing light from the light source toward two different directions;
   (d) two filters located on the way of light path and having different pass-bands from each other, one of which has a pass-band in which light transmittance level is relatively high with respect to the liquid to be detected while the other of which has a pass-band in which light transmittance level is relatively low with respect to the liquid to be detected;
   (e) two detecting means for detecting the light beam which has passed through the container and has been chopped and splitted;
   (f) a signal processor circuit in which each light quantity filtered by the two filters and received by the detecting means is converted into two electric signals which are compared with each other, said signal processor having two sample and hold circuits to which said two electronic signals are respectively transferred from the corresponding detecting means to hold the signals, a divider for dividing one of the two held signals by the other thereof and a signal generator for outputting a hold signal to the sample and hold circuits, said signal generator having a light illuminating element and a a light receiving element located on the opposite side of the chopper wheel so that the hold signal is generated when light emitted from the light illuminating element passes through a hole of the chopper wheel;
   (g) a shield plate located between the light source and the bottom of the container to be detected in order to permit the light beam projected from the light source to illuminate only the bottom of the container, said shield plate being provided an annular aperture for illuminating only the circumferential parts of the bottom of the container.

4. An apparatus according to claim 3, wherein said beam splitter has an oscillating mirror for directing the light beam alternately to each of the two detecting means disposed in a predetermined angular position with respect to the oscillating mirror, each of the filters being located between the oscillating mirror and the corresponding detecting means.

5. An apparatus for detecting residual liquid such as water, liquid soap or oil in containers, comprising:
   (a) light source located under the bottom of a container to be detected;
   (b) a rotatable combination filter for chopping the light from the light source and splitting it into two light beams, the combination filter being formed by combining two filter parts having different pass-bands from each other, one of which has a pass-band in which light transmittance level is relatively high with respect to the liquid to be detected while the other of which has a pass-band in which light transmittance level is relatively low with respect to the liquid to be detected;
   (c) means for detecting the light beam which has passed through the container and has been chopped and splitted;
   (d) a signal processor circuit in which each light quantity filtered by the two filters and received by the detecting means is converted into two electric signals which are compared with each other, said signal processor having two sample and hold circuits to which said two electronic signals are respectively transferred from the detecting means to hold the signals, a divider for dividing one of the two held signals by the other thereof and a signal generator for outputting a hold signal to the sample and hold circuits; and
   (e) a shield plate located between the light source and the bottom of the container to be detected in order to permit the light beam projected from the light source to illuminate only the bottom of the container, said shield plate being provided an annular aperture for illuminating only the circumferential parts of the bottom of the container.

6. An apparatus according to claim 5, wherein said chopping and splitting means has a rotatable chopper wheel with a plurality of holes located at predetermined intervals of length in its circumferential direction and a beam splitter for directing the light toward two different directions in which the respective detective elements are located, respectively, each of the filters being located between the beam splitter and the corresponding detecting element.

7. An apparatus according to claim 5, wherein said chopping and splitting means has an oscillating mirror for directing the light beam alternately to each of the two detecting elements disposed in a predetermined angular position with respect to the oscillating mirror, each of the filters being located between the oscillating mirror and the corresponding detecting element.

8. An apparatus according to claim 5, wherein said chopping and splitting means forms a part of rotatable combination filter which is formed by combining two filter parts corresponding to said two filters, the light beam chopped and splitted by the combination filter being received by one detecting element.

9. An apparatus according to claim 5, wherein said signal processor has two sample and hold circuits to which said two electronic signals are respectively transferred from the corresponding detecting element to hold the signals, a divider for dividing one of the two held signals by the other thereof and a signal generator for outputting a hold signal to the sample and hold circuits.

* * * * *